US012742215B2

(12) United States Patent
Shi et al.

(10) Patent No.: US 12,742,215 B2
(45) Date of Patent: Sep. 22, 2026

(54) METHODS AND KITS FOR DETECTING VIRUS

(71) Applicant: CITY UNIVERSITY OF HONG KONG, Kowloon (HK)

(72) Inventors: Peng Shi, Kowloon (HK); Zixun Wang, Kowloon (HK); Xi Zhao, Kowloon (HK); Xianglin Ji, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 638 days.

(21) Appl. No.: 18/308,620

(22) Filed: Apr. 27, 2023

(65) Prior Publication Data

US 2023/0349010 A1 Nov. 2, 2023

Related U.S. Application Data

(60) Provisional application No. 63/355,570, filed on Jun. 24, 2022, provisional application No. 63/335,365, filed on Apr. 27, 2022.

(51) Int. Cl.

| | |
|---|---|
| ***C12Q 1/6834*** | (2018.01) |
| ***C12Q 1/70*** | (2006.01) |
| *C12Q 1/6804* | (2018.01) |

(52) U.S. Cl.
CPC .......... *C12Q 1/701* (2013.01); *C12Q 1/6834* (2013.01); *C12Q 1/6804* (2013.01)

(58) Field of Classification Search
CPC .... A61K 2039/5256; A61K 2039/5258; C12N 15/70
See application file for complete search history.

(56) References Cited

PUBLICATIONS

Zheng et al. Vaccine 2009, vol. 27, pp. 5001-5007.*
Danielson et al. FEBS Letters, 2013, vol. 567, issue 17, pp. 1198-1205.*
Nasheri et al. Analytical Biochemistry, 2011, vol. 412, pp. 165-172.*

* cited by examiner

*Primary Examiner* — Bao Q Li
(74) *Attorney, Agent, or Firm* — Conley Rose, P.C.

(57) ABSTRACT

Disclosed herein are methods of detecting viruses and methods of making a diagnosis of viral infection, by using RNA and DNA probes. According to some embodiments of the present disclosure, the method is useful in detecting and diagnosing SARS-CoV-2 infection. Accordingly, also disclosed herein are a kit for detecting SARS-CoV-2.

5 Claims, No Drawings

Specification includes a Sequence Listing.

METHODS AND KITS FOR DETECTING VIRUS

CROSS-REFERENCE TO RELATED APPLICATIONS

This application relates to and claims the benefit of U.S. Provisional Application No. 63/335,365, filed Apr. 27, 2022, and U.S. Provisional Application No. 63/355,570, filed Jun. 24, 2022; the content of the application is incorporated herein by reference in its entirety.

SEQUENCE LISTING XML

The present application is being filed along with a Sequence Listing XML in electronic format. The Sequence Listing XML is provided as an XML file entitled HP0259US_P7001-US_seq listing, created Mar. 27, 2023, which is 22 Kb in size. The information in the electronic format of the Sequence Listing XML is incorporated herein by reference in its entirety.

FIELD OF THE INVENTION

The present disclosure in general relates to the field of disease diagnosis. More particularly, the present disclosure relates to novel methods of detecting and diagnosing viral infection, for example, severe acute respiratory syndrome coronavirus 2 (SARS-CoV-2) infection.

BACKGROUND OF THE INVENTION

2. Description of Related Art

SARS-CoV-2 has spread to the globe, causing great damage to both human health and societal stability. Since 2019, the virus has undergone several generations of mutations, from the initial virus to the current omicron variant. The resultant of SARS-CoV-2 also changed from fever, cough, dyspnea, etc. to lowly symptomatic or asymptomatic, which leads to a delay of isolation of the carriers and greatly increases the spread capability. Critically, however, this silent transmission has led to the infection of individuals who are at increased risk of severe illness due to age or pre-existing conditions such as obesity, diabetes, cancer, immunosuppression, and/or cardiac, pulmonary or kidney disease. These phenomena make it urgently to develop an efficient and accurate detection method to quick detect the virus thus limiting the contact of infection hazards and blocking its transmission between people.

Reverse transcription-quantitative polymerase chain reaction (RT-qPCR) based detection methods are the most stable and popular strategy to determine the virus infection, and are adopted by the World Health Organization (WHO) as a guidance of the diagnosis. However, the time-consuming multi-step sample preparation and the requirement of well-trained professionals hinder its detection efficiency and usage in different scenarios. Further, the modelling of the viral dynamics and the fast variant generation speed require more frequent testing with fast turnaround time to break the current pandemic. CRISPR (an acronym for "clustered regularly interspaced short palindromic repeats")-based COVID-19 detection kit was another early approved and applied strategy for rapid on-site test. It uses a one-tube reaction manner with isothermal amplification (e.g., reverse transcription loop-mediated isothermal amplification (RT-LAMP)), and accordingly does not require additional instrument. Nonetheless, the off-target effects of CRISPR and the varying degrees of tolerance to mismatches between the guide RNA and the target nucleotides of CRISPR/Cas effectors may affect the accuracy for nucleotide detection. Besides, the target virus RNA may undergo degradation due to various factors (e.g., sample preparation, carrying over nuclease, and/or environmental RNase), which lead to substantial false negative result and therefore erroneous diagnosis of infected cases.

Accordingly, there is a continuing interest in developing a novel method for detecting viruses in a simple, fast and versatile way.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the present disclosure is directed to a method of determining the presence or absence of a virus in a biological sample. The method comprises, (a) extracting ribonucleic acids (RNAs) from the biological sample;

(b) mixing the extracted RNAs of step (a) with a first RNA probe comprising a first sequence complementary to a RNA sequence of the virus;

(c) mixing the product of step (b) with a ribonuclease (RNase) to produce a plurality of double-stranded RNA (dsRNA) fragments independently about 18-26 base pairs in length;

(d) mixing the plurality of dsRNA fragments of step (c) with a second RNA probe, which comprises the first sequence, and a second sequence disposed at the 3'-end of the first sequence;

(e) subjecting the product of step (d) to a P19 protein of tombusvirus;

(f) adding a deoxyribonucleic acid (DNA) probe to the product of step (e), wherein the DNA probe comprises a third sequence complementary to the second sequence, and a reporter molecule linked to the third sequence; and (g) determining the presence or absence of the virus via detecting the signal of the reporter molecule.

According to some preferred embodiments, the method further comprises the following steps prior to step (e):

(d-1) heating the product of step (d) at 94-98° C. for 5-30 seconds;

(d-2) incubating the product of step (d-1) at 55-60° C. for 10-30 seconds; and (d-3) repeating steps (d-1) and (d-2) for at least three times.

According to some embodiments, the P19 protein of step (e) is immobilized on a substrate. In one exemplary embodiment, the P19 protein comprises the amino acid sequence of SEQ ID NO: 24. In another exemplary embodiment, the P19 protein comprises the amino acid sequence of SEQ ID NO: 25.

The second aspect of the present disclosure pertains to a method of making a diagnosis as to whether a subject is infected by a virus via a biological sample of the subject. The method comprises, (a) extracting RNAs from the biological sample;

(b) mixing the extracted RNAs of step (a) with a first RNA probe comprising a first sequence complementary to a RNA sequence of the virus;

(c) mixing the product of step (b) with a RNase to produce a plurality of dsRNA fragments independently about 18-26 base pairs in length;

(d) mixing the product of step (c) with a second RNA probe, which comprises the first sequence, and a second sequence disposed at the 3'-end of the first sequence;

(e) subjecting the product of step (d) to a P19 protein of tombusvirus;

(f) adding a DNA probe to the product of step (e), wherein the DNA probe comprises a third sequence complementary to the second sequence, and a reporter molecule linked to the third sequence;

(g) detecting the signal of the reporter molecule; and (h) making the diagnosis of the viral infection based on the result of step (g), wherein the detection of the signal indicates that the subject is infected by the virus.

According to some preferred embodiments, the method further comprises the following steps prior to step (e):

(d-1) heating the product of step (d) at 94-98° C. for 5-30 seconds;

(d-2) incubating the product of step (d-1) at 55-60° C. for 10-30 seconds; and (d-3) repeating steps (d-1) and (d-2) for at least three times.

According to some embodiments, the P19 protein of step (e) is immobilized on a substrate. In one exemplary embodiment, the P19 protein comprises the amino acid sequence of SEQ ID NO: 24. In another exemplary embodiment, the P19 protein comprises the amino acid sequence of SEQ ID NO: 25.

The subject may be a plant or an animal. Preferably, the subject is a mammal; more preferably, a human.

The virus suitable to be detected or diagnosed by the present method may be a DNA virus or a RNA virus. Preferably, the virus is a RNA virus.

According to some embodiments, the virus is SARS-CoV-2, in which the first RNA probe comprises the first sequence set forth in SEQ ID NO: 1, the second RNA probe comprises the first and second sequences respectively set forth in SEQ ID NOs: 1 and 5, and the DNA probe comprises the third sequence set forth in SEQ ID NO: 9. In one exemplary embodiment, the first RNA probe, the second RNA probe and the DNA probe respectively comprise the nucleotide sequences of SEQ ID NOs: 1, 13, and 17.

According to certain embodiments, the virus is SARS-CoV-2, in which the first RNA probe comprises the first sequence set forth in SEQ ID NO: 2, the second RNA probe comprises the first and second sequences respectively set forth in SEQ ID NOs: 2 and 6, and the DNA probe comprises the third sequence set forth in SEQ ID NO: 10. In one exemplary embodiment, the first RNA probe, the second RNA probe and the DNA probe respectively comprise the nucleotide sequences of SEQ ID NOs: 2, 14, and 18.

According to certain embodiments, the virus is SARS-CoV-2, in which the first RNA probe comprises the first sequence set forth in SEQ ID NO: 3, the second RNA probe comprises the first and second sequences respectively set forth in SEQ ID NOs: 3 and 7, and the DNA probe comprises the third sequence set forth in SEQ ID NO: 11. In one exemplary embodiment, the first RNA probe, the second RNA probe and the DNA probe respectively comprise the nucleotide sequences of SEQ ID NOs: 3, 15, and 19.

According to some embodiments, the virus is SARS-CoV-2, in which the first RNA probe comprises the first sequence set forth in SEQ ID NO: 4, the second RNA probe comprises the first and second sequences respectively set forth in SEQ ID NOs: 4 and 8, and the DNA probe comprises the third sequence set forth in SEQ ID NO: 12. In one exemplary embodiment, the first RNA probe, the second RNA probe and the DNA probe respectively comprise the nucleotide sequences of SEQ ID NOs: 4, 16, and 20.

Also disclosed herein is a kit for detecting SARS-CoV-2. The kit comprises, a P19 protein of tombusvirus;

a first to a fourth RNA probes respectively comprising the nucleotide sequences of SEQ ID NOs: 1-4;

a first to a fourth RNA fragments respectively comprising the nucleotide sequence of SEQ ID NOs: 13-16;

a first to a fourth DNA probes respectively comprising the nucleotide sequence of SEQ ID NOs: 17-20;

a first to a fourth reporter molecules respectively linked to the first to fourth DNA probes; and an instruction manual indicating how to use the P19 protein, the first to fourth RNA probes, the first to fourth RNA fragments, and the first to fourth DNA probes to detect the SARS-CoV-2.

In some optional embodiments, the kit of the present disclosure further comprises a control RNA probe, a control RNA fragment, a control DNA probe, and a fifth reporter molecules linked to the control DNA probe. According to one exemplary embodiment, the control RNA probe, control RNA fragment and control DNA probe respectively comprise the nucleotide sequences of SEQ ID NOs: 21-23.

Preferably, each of the first to the fifth reporter molecules is different from one another.

DETAILED DESCRIPTION OF THE INVENTION

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "probe" refers to a single-stranded oligonucleotide or polynucleotide that can be hybridized with a complementary single-stranded target sequence to form a double-stranded molecule (hybrid). The term "RNA probe" refers to a single-stranded RNA molecule that has a sequence partly or completely complementary to a "target RNA" (e.g., the viral RNA), and specifically hybridizes to the target RNA to form a double-stranded RNA (dsRNA). The term "DNA probe" refers a single-stranded DNA molecule that has a sequence partly or completely complementary to a RNA sequence (e.g., the barcode sequence of the second RNA probe of the present disclosure), and specifically hybridizes to the RNA sequence to form a DNA-RNA hybrid.

As used herein, the term "complementary" in the context of an oligonucleotide (i.e., a sequence of nucleotides, such as the sequence of the present RNA or DNA probe) refers to standard Watson/Crick base pairing rules; for example, the sequence "A-G-T" is complementary to the sequence "T-C-A". Complementarity may not be perfect; stable duplexes may contain mismatched base pairs, or degenerative or unmatched nucleotides. A person having ordinary skill in the art can determine duplex stability empirically considering a number of variables including, for example, the length of the oligonucleotide, base composition and sequence of the oligonucleotide, incidence of mismatched base pairs, ionic strength, other hybridization buffer components and conditions.

"Percentage (%) sequence identity" is defined as the percentage of nucleotides in a candidate sequence that are identical with the nucleotides in the specific nucleotide sequence, after aligning the sequences and introducing gaps, if necessary, to achieve the maximum percent sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two nucleotide sequences was carried out by computer program BLASTN (nucleotide-nucleotide BLAST) provided online by Nation Center for Biotechnology Information (NCBI). The percentage sequence identity of a given nucleotide sequence A to a given nucleotide sequence B (which can alternatively be phrased as a given nucleotide sequence A that has a certain % nucleotide sequence identity to a given nucleotide sequence B) is calculated by the formula as follows:

$$\frac{X}{Y} \times 100$$

where X is the number of nucleotides scored as identical matches by the sequence alignment program BLAST in that program's alignment of A and B, and where Y is the total number of nucleotides in A or B, whichever is shorter.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results determined by the present method, optionally together with other clinical characteristics, to arrive at a diagnosis (that is, the occurrence or nonoccurrence) of viral infection for the subject from which a sample was obtained and assayed. That such a diagnosis is "determined" is not meant to imply that the diagnosis is 100% accurate. Many biomarkers or test results are indicative of multiple conditions. The skilled clinician does not use biomarker or test results in an informational vacuum, but rather biomarkers or test results are used together with other clinical indicia to arrive at a diagnosis. Thus, the presence of a biomarker or a positive signal above a threshold indicates a greater likelihood of the occurrence of disease in the subject relative to the absence of the biomarker or a negative signal above the threshold.

The term "subject" refers to a plant or animal (e.g., a mammal) including the human species that is detectable by the kit and/or method of the present invention. The term "subject" is intended to refer to both the male and female gender unless one gender is specifically indicated.

II. Description of the Invention

The present disclosure is based, at least in part, on the development of a highly versatile and powerful technique for rapid, non-PCR and sensitive diagnosis of viruses (especially RNA viruses) with miniaturized instruments and simplified procedures in a reliable and timely manner. Accordingly, the present disclosure provides methods of detecting and diagnosis of virus via the novel technique.

II-1. Methods of Detecting Virus

The first aspect of the present disclosure is directed to a method of determining the presence or absence of a virus in a biological sample. The method comprises, (a) extracting RNAs from the biological sample;
(b) mixing the extracted RNAs of step (a) with a first RNA probe;
(c) mixing the product of step (b) with a RNase;
(d) mixing the product of step (c) with a second RNA probe;
(e) subjecting the product of step (d) to a P19 protein of tombusvirus;
(f) adding a DNA probe to the product of step (e), wherein the DNA probe comprises a reporter molecule; and
(g) determining the presence or absence of the virus via detecting the signal of the reporter molecule.

The virus suitable to be detected by the present method may be a DNA virus or a RNA virus. Preferably, the virus is a RNA virus, such as SARS-CoV-2.

Depending on intended purpose, the biological sample may be a whole blood sample, plasma sample, serum sample, cerebrospinal fluid (CSF) sample, saliva sample, urine sample, pharyngeal sample, synovial fluid sample, nasal sample, or any samples containing biological materials taken from a biological source (e.g., a human), for example, feces sample, sputum sample, bronchoalveolar lavage, or biopsy specimens. As could be appreciated, the source of the biological sample varies with the nature of the virus; for example, in the case when the virus is SARS-CoV-2, then the biological sample may be any of sputum sample, nasal sample (e.g., nasal swab or nasal mucus), pharyngeal sample (e.g., pharyngeal swab), whole blood sample, feces sample, bronchoalveolar lavage, or bronchoscope brush biopsy specimens; and in the case when the virus is dengue virus, then the biological sample may be any of whole blood sample, serum sample, plasma sample, or CSF sample.

In step (a), RNAs are extracted from the biological sample. The RNAs may be extracted by any extraction methods known in the art, for example, guanidinium-acid-phenol extraction, silica-based glass fiber filters, spin columns, density gradient centrifugation using cesium chloride or cesium trifluoroacetate, magnetic beads, lithium chloride and urea isolation, cellulose column chromatography, and polyA isolation. The methods of extraction RNA are known in the art; hence, the detailed description thereof is omitted herein for the sake of brevity.

In step (b), the extracted RNAs of step (a) are mixed with a first RNA probe (hereinafter as a "capture probe"). According to the embodiments of the present disclosure, the capture probe comprises a nucleotide sequence (i.e., a capture sequence) complementary to a target RNA sequence of the virus. Accordingly, in the case when the virus is present in the biological sample, then the capture probe would specifically recognizes and binds to the target RNA sequence extracted in step (a), and forms a dsRNA therewith under a hybridization condition (e.g., incubating at 55-65° C. for least 1 hour). In contrast, in the case when the virus is absent in the biological sample, then no dsRNA would be formed in the step. According to some preferred embodiments of the present disclosure, the capture probe has about 20-30 nucleotides in length, for example, 20, 21, 22, 23, 24, 25, 26, 27, 28, 29 or 30 nucleotides. In one exemplary embodiment, the capture probe has 26 nucleotides in length.

In step (c), the product of step (b) is mixed with a RNase. According to the embodiments of the present disclosure, the treatment of the RNase under a suitable condition (e.g., incubating at 37° C. for 20 minutes) digests the dsRNA formed in step (b) into a plurality dsRNA fragments, each of which independently has about 18-26 base pairs (bps) in length. According to some exemplary embodiments, the RNase is SHORTCUT® RNase.

Then, in step (d), the dsRNA fragments of step (c) are mixed with a second RNA probe (hereinafter as a "RNA barcode probe"). According to the embodiments of the present disclosure, the RNA barcode probe in its structure comprises a capture sequence, and a barcode sequence linked to the 5'-end or 3'-end of the capture sequence. Depending on desired purpose, the barcode sequence may be linked to the capture sequence via one or more additional nucleotides (i.e., linking nucleotides); alternatively, the barcode sequence may be linked to the capture sequence without any linking nucleotides. In one exemplary embodiment, the barcode sequence is connected to the 3'-end of the capture sequence without any linking nucleotides disposed therebetween. The employment of the capture sequence allows the RNA barcode probe to displace the capture probe and hybridize with the target RNA sequence of the virus via chain displacement reaction. The thus-obtained dsRNA fragment has an overhang sequence (i.e., the barcode sequence).

According to some preferred embodiments of the present disclosure, the chain displacement reaction is performed by heating and annealing the product of step (d) for 3-15 cycles; preferably, 4-15 cycles; more preferably, 5-15 cycles. In some exemplary examples, the chain displacement reaction is performed by, (d-1) heating the product of step (d) at 94-98° C. (e.g., 94° C., 95° C., 96° C., 97° C. or 98° C.) for 5-30 seconds (e.g., 5, 6, 7, 8, 9, 10, 11, 12, 13, 14, 15, 16, 17, 18, 19, 20, 21, 22, 23, 24, 25, 26, 27, 28, 29 or 30 seconds);

(d-2) incubating the product of step (d-1) at 55-60° C. (e.g., 55° C., 56° C., 57° C., 58° C., 59° C. or 60° C.) for 10-30 seconds (e.g., 10, 11, 12, 13, 14, 15, 16, 17, 18, 19, 20, 21, 22, 23, 24, 25, 26, 27, 28, 29 or 30 seconds); and (d-3) repeating steps (d-1) and (d-2) for at least three times (e.g., 3, 4, 5, 6, 7, 8, 9, 10, 11, 12, 13, 14, 15, or more times).

According to working example, the chain displacement reaction is performed by heating the product of step (d) at 95° C. for 5-10 seconds followed by incubating at 55° C. for 10-30 seconds, for 5-15 cycles.

In step (e), the product of step (d) is subjected to a P19 protein, which recognizes and binds to dsRNA fragments. According to some embodiments of the present disclosure, the P19 protein is derived from tombusvirus, e.g., Tomato bushy stunt virus (TBSV). In one exemplary embodiment, the P19 protein comprises the amino acid sequence of "MERAIQGNDAREQANSERWDGGS GSSTSPFQL-PDESPSWTEWRLHNDETNSNQDNPL GFKESWG-FGKVVFKRYLRYERTETSLHRVLGSWTGDSV-NYAASRFFGVNQIGCTYSIRF RGVSVTISGGSRTLQ-HLCEMAIRSKQELLQLTPVEVESNVSRGCPEGVET-FEEESE" (SEQ ID NO: 24). In another exemplary embodiment, the P19 protein comprises the amino acid sequence of "MERAIQGNDAREQANSERWDGGSGGTTSPFKLP-DESPSWTEWRLHNDET NSNQDNPLGFKESWG-FGKVVFKRYLRYDRTEASLHRVLGSWTGDS-VNYAASRFFGFD QIGCTYSIRFRGVSITVSGGSRTL-QHLCEMAIRSKQELLQLAPIEVESNVSRGCPEG-TETFE KESE" (SEQ ID NO: 25).

Optionally, the P19 protein is immobilized on a substrate. The substrate may be any materials which can be coupled with a molecule with low background noise. Conventionally, the substrate may be a microtiter plate, a membrane (e.g., nylon or nitrocellulose), a microsphere (e.g., bead), a chip, or a nanoneedle. According to certain embodiments, the P19 protein is immobilized on a nanoneedle array, i.e., an array of nanoneedles substantially aligned perpendicular to a supporting base.

Optionally, the method further comprises washing the product of (e) with a wash buffer (such as sodium dodecyl sulfate (SDS) buffer) that removes unbound molecules (e.g., unbound dsRNA fragments).

In step (f), a DNA probe (hereinafter as a "DNA barcode probe") is added to the product of step (e). According to the embodiments of the present disclosure, the DNA barcode probe in its structure comprises a nucleotide sequence (i.e., a complementary barcode sequence) that is complementary to the barcode sequence of the RNA barcode probe, and a reporter molecule linked to the complementary barcode sequence. Depending on desired purpose, the reporter molecule may be linked to the complementary barcode sequence via one or more additional nucleotides (i.e., linking nucleotides); alternatively, the reporter molecule may be linked to the complementary barcode sequence without any linking nucleotides. In one exemplary embodiment, the reporter molecule is linked to the 5'-end of the complementary barcode sequence with a linker sequence consisting of six thymine (T). A skilled artisan may choose a suitable linker nucleotide or sequence in accordance with practical requirements. The DNA barcode probe recognizes and specifically binds to the RNA barcode probe via the interaction between the complementary barcode sequence of the DNA barcode probe and the barcode sequence of the RNA barcode probe.

Depending on intended purpose, the reporter molecule may be a fluorescent molecule (e.g., green-fluorescent dye, yellow-fluorescent dye, red-fluorescent dye or blue-fluorescent dye), a phosphorescent molecule (e.g, zinc sulfide or strontium aluminate), a chemiluminescent molecule (e.g., luciferin or luminol), a tag molecule (e.g, biotin, avidin, or streptavidin), or an enzyme (e.g, horseradish peroxidase, HRP).

Optionally, the method further comprises washing the product of (f) with a wash buffer (such as SDS buffer) that removes unbound molecules (e.g., unbound DNA barcode probe).

Next, in step (g), the presence or absence of the virus in the biological sample is determined via detecting the signal of the reporter molecule of the DNA barcode probe. Specifically, the detection of the signal indicates that the virus is present in the biological sample; in contrast, no signal or a signal under a predetermined threshold indicates that the virus is absent or is negligible in the biological sample.

As would be appreciated, the method for detecting the signal of the reporter molecule may vary with the type of the reporter molecule used. For example, when the reporter molecule is a fluorescent molecule, the signal may be detected or quantified by a fluorescence detector (e.g., flow cytometry or fluorescence microscope). Alternatively, in the case when the reporter molecule is an enzyme, the signal may be detected or quantified by interacting with an enzyme substrate, which is then catalyzed/degraded by the enzyme and converted into a colored product.

According to certain embodiments of the present disclosure, the method is useful in detecting SARS-CoV-2 and/or its variants. In these embodiments, four sets of probes are provided as exemplary implementations of the present invention, and the nucleotide sequences thereof are summarized in Table 1.

TABLE 1

Nucleotide sequences of specified probes

| Probe set | Probe name | Nucleotide sequence[1,2,3] | SEQ ID NO[4] |
|---|---|---|---|
| 1 | Capture probe | UAUAAUGUCUCCUACAACUUCGGUAG | 1 |
| | RNA barcode probe | UAUAAUGUCUCCUACAACUUCGGUAG<br>**CUGAGAUCCCAA** | 13 |
| | DNA barcode probe | TTTTTT*TTGGGATCTCAG* | 17 |
| 2 | Capture probe | ACUAGCAUUGUCUACAUAAGCAGCCA | 2 |
| | RNA barcode probe | ACUAGCAUUGUCUACAUAAGCAGCCA<br>**CCAAUGGAGAAU** | 14 |
| | DNA barcode probe | TTTTTT*ATTCTCCATTGG* | 18 |
| 3 | Capture probe | AAACAAUCUAUACCGGUAAUUAUAAU | 3 |
| | RNA barcode probe | AAACAAUCUAUACCGGUAAUUAUAAU<br>**AUACCUCAAGUG** | 15 |
| | DNA barcode probe | TTTTTT*CACTTGAGGTAT* | 19 |
| 4 | Capture probe | ACCAUUACAAGGUUUGCUACCGGCCU | 4 |
| | RNA barcode probe | ACCAUUACAAGGUUUGCUACCGGCCU<br>**UGCCCAGUGAGA** | 16 |
| | DNA barcode probe | TTTTTT*TCTCACTGGGCA* | 20 |

[1]The barcode sequence of each RNA barcode probe is indicated in boldface, including the nucleotide sequence "CUGAGAUCCCAA" (SEQ ID NO: 5) of the first probe set, the nucleotide sequence "CCAAUGGAGAAU" (SEQ ID NO: 6) of the second probe set, the nucleotide sequence "AUACCUCAAGUG" (SEQ ID NO: 7) of the third probe set, and the nucleotide sequence "UGCCCAGUGAGA" (SEQ ID NO: 8) of the fourth probe set.

[2]The complementary barcode sequence of each DNA barcode probe is indicated in italic font, including the nucleotide sequence "TTGGGATCTCAG" (SEQ ID NO: 9) of the first probe set, the nucleotide sequence "ATTCTCCATTGG" (SEQ ID NO: 10) of the second probe set, the nucleotide sequence "CACTTGAGGTAT" (SEQ ID NO: 11) of the third probe set, and the nucleotide sequence "TCTCACTGGGCA" (SEQ ID NO: 12) of the fourth probe set.

[3]Each DNA barcode probe comprises a linker consisting of six thymine (T) disposed at the 5'-end of the complementary barcode sequence.

[4]Under WIPO ST.26, "t" represents uracil in RNA sequences.

II-2. Methods of Diagnosing Viral Infection

The second aspect of the present disclosure pertains to a method of making a diagnosis as to whether a subject is infected by a virus (e.g., a DNA virus or RNA virus) via a biological sample of the subject. The method comprises, (a) extracting RNAs from the biological sample;
(b) mixing the extracted RNAs of step (a) with a first RNA probe;
(c) mixing the product of step (b) with a RNase;
(d) mixing the product of step (c) with a second RNA probe;
(e) subjecting the product of step (d) to a P19 protein of tombusvirus;
(f) adding a DNA probe to the product of step (e), wherein the DNA probe comprises a reporter molecule;
(g) detecting the signal of the reporter molecule; and
(h) making the diagnosis of the viral infection based on the result of step (g).

The steps (a) to (g) of the diagnostic method are quite similar to that of the detecting method as described in Section II-1 of the present disclosure. Thus, the detailed description thereof is omitted herein for the sake of brevity.

In step (h), a skilled artisan or a clinical practitioner may make a diagnosis as to whether the subject is infected by the virus based on the detecting result of step (g), in which the detection of the signal indicates that the subject is infected by the virus; in contrast, no signal or a signal under a predetermined threshold indicates that the subject is not infected by the virus and/or is not affected by the virus (exhibiting no symptoms commonly associated with the virus).

Based on the result, a skilled artisan or a clinical practitioner may administer to a subject in need thereof (e.g., a subject infected by the virus) an appropriate treatment in time. Specifically, in the case when the subject is infected by the virus (e.g., SARS-CoV-2), then an effective amount of an anti-viral treatment (e.g., an anti-SARS-CoV-2 agent, such as tocilizumab, remdesivir, baricitinib, ritonavir, nirmatrelvir, molnupiravir, anakinra, infeterron-alpha (IFN-α), IFN-β, or a combination thereof) is administered to the subject so as to alleviate and/or ameliorate the symptoms associated with viral infection.

The subject may be a plant or an animal (e.g., a mammal or domesticated bird). Preferably, the subject is a mammal; for example, a human, monkey, mouse, rat, cat, dog, cow, horse, pig, goat, sheep or rabbit. More preferably, the subject is a human.

Compared to the traditional technology or product, the present method is advantageous in, (1). No amplification procedure is required, thus reducing the infection risk and saving time;
(2). Simple steps and very fast detection;
(3). Small RNA fragments detection capability;
(4). High detection accuracy and no off-target effect, thus reducing the false negative result;
(5). P19-protein-based strategy is capable of reliably discriminate different Covid-19 variants at single bp mutation without RNA sequencing;
(6). Capable of distinguishing different lineage while enhancing detection sensitivity via targeting multiple regions of the viral sequence;
(7). Quantitatively detecting SARS-CoV-2 and variants without pre-amplification;
(8). Improved detection capability for handling low quality samples by using about 20-30 bp RNA probes for detection;
(9). Simple step and fast detection with adequate detection limitation and no off-target effect; and
(10). Digitalized nanoimaging for copy number quantification with versatile application capability in many RNA target detections.

According to some embodiments of the present disclosure, the present invention provides a highly versatile and powerful technique for fast, non-PCR, highly sensitive detection of viral RNA. The present RNA detection method can be applied for fast and early diagnosis of various viral infection, and can be easily converted to different detection kits to cope with the emergence of different viruses and viral variants.

II-3. Kits for Detecting SARS-CoV-2

The third aspect of the present disclosure provides a kit for detecting SARS-CoV-2. According to certain embodiments of the present disclosure, the kit comprises a P19 protein, four sets of probes (including four sets of capture probes, RNA barcode probes and DNA barcode probes) as summarized in Table 1 above, and an instruction manual indicating how to use the P19 protein and probes to detect SARS-CoV-2.

According to certain embodiments, the P19 protein is derived from tombusvirus, e.g., TBSV. In one exemplary embodiment, the P19 protein comprises the amino acid sequence of SEQ ID NO: 24. In another exemplary embodiment, the P19 protein comprises the amino acid sequence of SEQ ID NO: 25.

Optionally, in addition to the four sets of probes, the kit further comprises a fifth set of probes serving as negative controls. According to some embodiments, the fifth set of probes includes a control capture probe, a control RNA barcode probe and a control DNA barcode probe. In certain exemplary embodiments, the control RNA probe, control RNA fragment and control DNA probe respectively comprise the nucleotide sequences of SEQ ID NOs: 21-23 as summarized in Table 2.

TABLE 2

Nucleotide sequences of specified probes

| Probe set | Probe name | Nucleotide sequence[1,2] | SEQ ID NO[3] |
|---|---|---|---|
| 5 | Control capture probe | UCACCGGGUGUAAAUCAGCUUG | 21 |
| | Control RNA barcode probe | AGCUGAUUUACACCCGGUGA **CCUGGAGUCAGU** | 22 |
| | Control DNA barcode probe | TTTTTT*ACTGACTCCAGG* | 23 |

[1]The barcode sequence of the control RNA barcode probe is indicated in boldface, and the complementary barcode sequence of the control DNA barcode probe is indicated in italic font.
[2]The control DNA barcode probe comprises a linker consisting of six thymine (T) disposed at the 5'-end of the complementary barcode sequence.
[3]Under WIPO ST.26, "t" represents uracil in RNA sequences.

According to some embodiments, each of the DNA barcode probes is conjugated with a reporter molecule, which, as described above, may be a fluorescent molecule, phosphorescent molecule, chemiluminescent molecule, tag molecule, or enzyme. In certain exemplary embodiments, each of the reporter molecules is a biotin tag, which is linked to the complementary barcode sequence of the DNA barcode probe via a linker sequence (e.g., a linker sequence consisting of six T nucleotides), and the signal is detected by adding avidin-conjugated or streptavidin-conjugated fluorophore. Preferably, each of the fluorophores respectively linked to the DNA barcode probes is different from one another. In alternative embodiments, the reporter molecule is fluorescent molecule.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example

Materials and Methods

Probe Synthesis

The present probes (including DNA probes and RNA probes) were produced by solid-phage synthesis. Five sets of probes were provided in the present study, in which (1) the first set of probe included a capture probe of SEQ ID NO: 1, a RNA barcode probe of SEQ ID NO: 13, and a DNA barcode probe of SEQ ID NO: 17;

(2) the second set of probe included a capture probe of SEQ ID NO: 2, a RNA barcode probe of SEQ ID NO: 14, and a DNA barcode probe of SEQ ID NO: 18;

(3) the third set of probe included a capture probe of SEQ ID NO: 3, a RNA barcode probe of SEQ ID NO: 15, and a DNA barcode probe of SEQ ID NO: 19;

(4) the fourth set of probe included a capture probe of SEQ ID NO: 4, a RNA barcode probe of SEQ ID NO: 16, and a DNA barcode probe of SEQ ID NO: 20; and (5) the fifth set of probe (control probes) included a capture probe of SEQ ID NO: 21, a RNA barcode probe of SEQ ID NO: 22, and a DNA barcode probe of SEQ ID NO: 23.

For the purpose of conjugating with a fluorophore, each DNA barcode probe included a biotin tag conjugated to its 5'-end.

Functionalization of Nanoneedles

To functionalize the nanoneedles with P19 protein, a patch were first bathed in piranha (3:1, v/v, 98% $H_2SO_4$: 27.5% $H_2O_2$) solution at 90° C. for 1.5 hours and then cleaned by distilled water, methanol, methanol/dichloride methane (DCM) mixture (3:1, v/v), and DCM sequentially. The nanoneedle patch was dried with nitrogen and then immersed in (3-Aminopropyl)triethoxysilane (APTES) solution (20% in DCM, v/v) overnight in a nitrogen protected environment. Ethanol, isopropyl alcohol, and distilled water were sequentially used to rinse the nanoneedle patch, which was further dried by nitrogen blow. The nanoneedle patch was then bathed in NHS-biotin solution (1 μg/mL in phosphate buffered saline (PBS)) for 1 hour, streptavidin solution (10 μg/mL in PBS) for 2 hours, and biotinylated P19 siRNA binding protein solution (1 μg/mL in PBS) for 1 hour. The nanoneedle patch was rinsed with distilled water between adjacent bath steps.

After each experiment, the nanoneedle patch was soaked in hot (about 90° C.) piranha solution (3:1, v/v, 98% $H_2SO_4$: 27.5% $H_2O_2$) to remove all crosslinked materials (protein, nucleotides, etc.) on the nanoneedle surface, and scanning electron microscope (SEM) images were taken ensure the integrity of the nanoneedle structure. In this way, one patch can be used for at least 20 times.

Fluorescent Beads Fabrication

50 μL amino magnetic beads (300-400 nm diameter, in PBS) were used for the spectrum codes preparation followed by reacting with 1 μL biotin-NHS (2 mg/mL) for 2 hours in room temperature. Then, the beads were washed 3 times using DEPC-PBS (PBS containing diethyl pyrocarbonate), and 5 μL diverse type of streptavidin-conjugated fluorophores (including streptavidin-conjugated ALEXA FLUOR™ 488, streptavidin-conjugated ALEXA FLUOR™ 514, streptavidin-conjugated ALEXA FLUOR™ 555, and streptavidin-conjugated ALEXA FLUOR™ 647, 2 mg/mL) were mixed together with biotin functionalized beads for 2 hours in room temperature. The beads were washed with DEPC-PBS 3 times, and 4 μL corresponding biotin DNA probe (100 μM) was mixed with the beads for 2 hours, followed by treating with unlabeled biotin (0.1 mg/mL) for another 2 hours to block the unreacted streptavidin. After washing three times with DEPC-PBS, the beads were dispersed in 50 μL 1% bovine serum albumin (BSA) and 0.1% TRITON®-X100 solution and stored in 4° for further applications.

Example 1 Detecting SARS-CoV-2 by the Present Method

The samples (including mock RNA sample and clinical samples) were mixed with capture probes, followed by incubating at 95° C. for 1 minute. The SHORTCUT® RNase was added to the sample. After incubating at 37° C. for 30 minutes, ethylenediaminetetraacetic acid (EDTA) was added into the reaction to stop the enzyme digestion. Then, RNA barcode probes with specifically overhang sequences were added into the reaction system. The product was subjected to a heating and cooling (denaturing and annealing) cycles, i.e., heating at 95° C. for 5-10 seconds and annealing at 55° C. for 10-30 seconds for 5-15 cycles, so as to ensure the chain displacement.

The thus-obtained dsRNA fragments were incubated with the P19 functionalized nanoneedle chip. The specific fluorescent beads were used to identify the overhang sequence that emitted fluorescence under fluorescent microscope. The results confirmed that the present method was useful in detecting SARS-CoV-2 (data not shown).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of determining the presence or absence of an RNA virus in a biological sample, comprising,
   (a) extracting ribonucleic acids (RNAs) from the biological sample;
   (b) mixing the extracted RNAs of step (a) with a first RNA probe comprising a first sequence complementary to a RNA sequence of the virus, wherein the first RNA probe comprises the first sequence set forth in SEQ ID NO: 1;
   (c) mixing the product of step (b) with a ribonuclease (RNase) to produce a plurality of double-stranded RNA (dsRNA) fragments independently 18-26 base pairs in length;
   (d) mixing the plurality of dsRNA fragments of step (c) with a second RNA probe, which comprises the first sequence, and a second sequence disposed at the 3'-end of the first sequence, wherein the second RNA probe comprises the first and second sequences respectively set forth in SEQ ID NOs: 1 and 5;
   (e) subjecting the product of step (d) to a P19 protein of tombusvirus;
   (f) adding a deoxyribonucleic acid (DNA) probe to the product of step (e), wherein the DNA probe comprises a third sequence complementary to the second sequence, and a reporter molecule linked to the third sequence, in which the DNA probe comprises the third sequence set forth in SEQ ID NO: 9; and
   (g) determining the presence or absence of the RNA virus via detecting the signal of the reporter molecule;
   wherein, the RNA virus is severe acute respiratory syndrome coronavirus-2 (SARS-CoV-2).

2. The method of claim 1, further comprising the following steps prior to step (e):
   (d-1) heating the product of step (d) at 94-98° C. for 5-30 seconds;
   (d-2) incubating the product of step (d-1) at 55-60° C. for 15-30 seconds; and
   (d-3) repeating steps (d-1) and (d-2) for at least three times.

3. The method of claim 1, wherein the P19 protein comprises the amino acid sequence of SEQ ID NO: 24.

4. The method of claim 1, wherein the P19 protein is immobilized on a substrate.

5. The method of claim 1, wherein
   the first RNA probe, the second RNA probe and the DNA probe respectively comprise the nucleotide sequences of SEQ ID NOs: 1, 13, and 17.

* * * * *

SEQUENCE LISTING

```
Sequence total quantity: 25
SEQ ID NO: 1            moltype = RNA  length = 26
FEATURE                 Location/Qualifiers
source                  1..26
                        mol_type = other RNA
                        organism = synthetic construct
SEQUENCE: 1
```

```
tataatgtct cctacaactt cggtag                                            26

SEQ ID NO: 2             moltype = RNA  length = 26
FEATURE                  Location/Qualifiers
source                   1..26
                         mol_type = other RNA
                         organism = synthetic construct
SEQUENCE: 2
actagcattg tctacataag cagcca                                            26

SEQ ID NO: 3             moltype = RNA  length = 26
FEATURE                  Location/Qualifiers
source                   1..26
                         mol_type = other RNA
                         organism = synthetic construct
SEQUENCE: 3
aaacaatcta taccggtaat tataat                                            26

SEQ ID NO: 4             moltype = RNA  length = 26
FEATURE                  Location/Qualifiers
source                   1..26
                         mol_type = other RNA
                         organism = synthetic construct
SEQUENCE: 4
accattacaa ggtttgctac cggcct                                            26

SEQ ID NO: 5             moltype = RNA  length = 12
FEATURE                  Location/Qualifiers
source                   1..12
                         mol_type = other RNA
                         organism = synthetic construct
SEQUENCE: 5
ctgagatccc aa                                                           12

SEQ ID NO: 6             moltype = RNA  length = 12
FEATURE                  Location/Qualifiers
source                   1..12
                         mol_type = other RNA
                         organism = synthetic construct
SEQUENCE: 6
ccaatggaga at                                                           12

SEQ ID NO: 7             moltype = RNA  length = 12
FEATURE                  Location/Qualifiers
source                   1..12
                         mol_type = other RNA
                         organism = synthetic construct
SEQUENCE: 7
atacctcaag tg                                                           12

SEQ ID NO: 8             moltype = RNA  length = 12
FEATURE                  Location/Qualifiers
source                   1..12
                         mol_type = other RNA
                         organism = synthetic construct
SEQUENCE: 8
tgcccagtga ga                                                           12

SEQ ID NO: 9             moltype = DNA  length = 12
FEATURE                  Location/Qualifiers
source                   1..12
                         mol_type = other DNA
                         organism = synthetic construct
SEQUENCE: 9
ttgggatctc ag                                                           12

SEQ ID NO: 10            moltype = DNA  length = 12
FEATURE                  Location/Qualifiers
source                   1..12
                         mol_type = other DNA
                         organism = synthetic construct
SEQUENCE: 10
attctccatt gg                                                           12

SEQ ID NO: 11            moltype = DNA  length = 12
FEATURE                  Location/Qualifiers
source                   1..12
                         mol_type = other DNA
                         organism = synthetic construct
```

```
SEQUENCE: 11
cacttgaggt at                                                 12

SEQ ID NO: 12           moltype = DNA  length = 12
FEATURE                 Location/Qualifiers
source                  1..12
                        mol_type = other DNA
                        organism = synthetic construct
SEQUENCE: 12
tctcactggg ca                                                 12

SEQ ID NO: 13           moltype = RNA  length = 38
FEATURE                 Location/Qualifiers
source                  1..38
                        mol_type = other RNA
                        organism = synthetic construct
SEQUENCE: 13
tataatgtct cctacaactt cggtagctga gatcccaa                     38

SEQ ID NO: 14           moltype = RNA  length = 38
FEATURE                 Location/Qualifiers
source                  1..38
                        mol_type = other RNA
                        organism = synthetic construct
SEQUENCE: 14
actagcattg tctacataag cagccaccaa tggagaat                     38

SEQ ID NO: 15           moltype = RNA  length = 38
FEATURE                 Location/Qualifiers
source                  1..38
                        mol_type = other RNA
                        organism = synthetic construct
SEQUENCE: 15
aaacaatcta taccggtaat tataatatac ctcaagtg                     38

SEQ ID NO: 16           moltype = RNA  length = 38
FEATURE                 Location/Qualifiers
source                  1..38
                        mol_type = other RNA
                        organism = synthetic construct
SEQUENCE: 16
accattacaa ggtttgctac cggccttgcc cagtgaga                     38

SEQ ID NO: 17           moltype = DNA  length = 18
FEATURE                 Location/Qualifiers
source                  1..18
                        mol_type = other DNA
                        organism = synthetic construct
SEQUENCE: 17
ttttttttgg gatctcag                                           18

SEQ ID NO: 18           moltype = DNA  length = 18
FEATURE                 Location/Qualifiers
source                  1..18
                        mol_type = other DNA
                        organism = synthetic construct
SEQUENCE: 18
ttttttattc tccattgg                                           18

SEQ ID NO: 19           moltype = DNA  length = 18
FEATURE                 Location/Qualifiers
source                  1..18
                        mol_type = other DNA
                        organism = synthetic construct
SEQUENCE: 19
ttttttcact tgaggtat                                           18

SEQ ID NO: 20           moltype = DNA  length = 18
FEATURE                 Location/Qualifiers
source                  1..18
                        mol_type = other DNA
                        organism = synthetic construct
SEQUENCE: 20
tttttttctc actgggca                                           18

SEQ ID NO: 21           moltype = RNA  length = 22
FEATURE                 Location/Qualifiers
source                  1..22
                        mol_type = other RNA
```

-continued

```
                       organism = synthetic construct
SEQUENCE: 21
tcaccgggtg taaatcagct tg                                        22

SEQ ID NO: 22          moltype = RNA  length = 32
FEATURE                Location/Qualifiers
source                 1..32
                       mol_type = other RNA
                       organism = synthetic construct
SEQUENCE: 22
agctgattta cacccggtga cctggagtca gt                             32

SEQ ID NO: 23          moltype = DNA  length = 18
FEATURE                Location/Qualifiers
source                 1..18
                       mol_type = other DNA
                       organism = synthetic construct
SEQUENCE: 23
tttttactg actccagg                                              18

SEQ ID NO: 24          moltype = AA  length = 172
FEATURE                Location/Qualifiers
source                 1..172
                       mol_type = protein
                       organism = synthetic construct
SEQUENCE: 24
MERAIQGNDA REQANSERWD GGSGSSTSPF QLPDESPSWT EWRLHNDETN SNQDNPLGFK  60
ESWGFGKVVF KRYLRYERTE TSLHRVLGSW TGDSVNYAAS RFFGVNQIGC TYSIRFRGVS  120
VTISGGSRTL QHLCEMAIRS KQELLQLTPV EVESNVSRGC PEGVETFEEE SE          172

SEQ ID NO: 25          moltype = AA  length = 172
FEATURE                Location/Qualifiers
source                 1..172
                       mol_type = protein
                       organism = synthetic construct
SEQUENCE: 25
MERAIQGNDA REQANSERWD GGSGGTTSPF KLPDESPSWT EWRLHNDETN SNQDNPLGFK  60
ESWGFGKVVF KRYLRYDRTE ASLHRVLGSW TGDSVNYAAS RFFGFDQIGC TYSIRFRGVS  120
ITVSGGSRTL QHLCEMAIRS KQELLQLAPI EVESNVSRGC PEGTETFEKE SE          172
```